(12) United States Patent
Pribanic et al.

(10) Patent No.: US 8,734,469 B2
(45) Date of Patent: May 27, 2014

(54) SUTURE CLIP APPLIER

(75) Inventors: Russell Pribanic, Roxbury, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 321 days.

(21) Appl. No.: 12/897,868

(22) Filed: Oct. 5, 2010

(65) Prior Publication Data
US 2011/0087242 A1 Apr. 14, 2011

Related U.S. Application Data

(60) Provisional application No. 61/250,894, filed on Oct. 13, 2009.

(51) Int. Cl.
*A61B 17/10* (2006.01)

(52) U.S. Cl.
USPC ............ 606/142; 606/136; 606/143; 606/232

(58) Field of Classification Search
USPC ......... 606/139, 142, 143, 151, 157, 158, 213, 606/232; 623/23.72
See application file for complete search history.

(56) References Cited

U.S. PATENT DOCUMENTS

| | | |
|---|---|---|
| 3,120,230 A | 2/1964 | Skold |
| 3,638,847 A | 2/1972 | Noiles et al. |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |

(Continued)

FOREIGN PATENT DOCUMENTS

| | | |
|---|---|---|
| DE | 20 2009 006113 | 7/2009 |
| EP | 0 085 931 A2 | 8/1983 |

(Continued)

OTHER PUBLICATIONS

Extended European Search Report corresponding to EP 10252079.8, date of mailing is Mar. 17, 2011; date of completion of Search is Mar. 8, 2011 (3 Pages).

(Continued)

*Primary Examiner* — Corrine M McDermott
*Assistant Examiner* — Jing Ou

(57) ABSTRACT

Suture clip appliers, suture clips and methods of their use for securing sutures during an endoscopic or laparoscopic procedure are provided, wherein the method includes the steps of providing a suture clip applier having a working tip configured to retain and fire a suture clip; providing a suture clip having a biased closed configuration; loading the suture clip into the working tip of the clip applier; translating the suture clip distally relative to the working tip to a first position wherein the suture clip is splayed open; inserting a suture into the opened suture clip; and translating the suture clip distally relative to the working tip such that the suture clip is ejected from the working tip and biased to the closed configuration to close on and to retain the suture.

15 Claims, 9 Drawing Sheets

(56) References Cited

U.S. PATENT DOCUMENTS

| | | |
|---|---|---|
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry |
| 5,382,255 A | 1/1995 | Castro |
| 5,383,881 A | 1/1995 | Green |
| 5,395,375 A | 3/1995 | Turkel et al. |
| 5,395,381 A | 3/1995 | Green |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green |
| 5,425,740 A | 6/1995 | Hutchinson, Jr. |
| 5,431,667 A | 7/1995 | Thompson |
| 5,431,668 A | 7/1995 | Burbank, III et al. |
| 5,431,669 A | 7/1995 | Thompson |
| 5,439,468 A | 8/1995 | Schulze et al. |
| 5,441,509 A | 8/1995 | Vidal |
| 5,447,513 A * | 9/1995 | Davison et al. ................ 606/143 |
| 5,449,365 A | 9/1995 | Green |
| 5,462,555 A | 10/1995 | Bolanos |
| 5,462,558 A | 10/1995 | Kolesa |
| 5,464,416 A | 11/1995 | Steckel |
| 5,474,566 A | 12/1995 | Alesi |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips |

(56) References Cited

U.S. PATENT DOCUMENTS

| | | |
|---|---|---|
| 5,514,149 A | 5/1996 | Green |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green |
| 5,527,320 A | 6/1996 | Carruthers et al. |
| 5,542,949 A | 8/1996 | Yoon |
| 5,547,474 A | 8/1996 | Kloeckl |
| 5,569,274 A | 10/1996 | Rapacki et al. |
| 5,571,121 A | 11/1996 | Heifetz |
| 5,575,802 A | 11/1996 | McQuildin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt |
| 5,618,291 A | 4/1997 | Thompson |
| 5,618,306 A | 4/1997 | Roth et al. |
| 5,620,452 A | 4/1997 | Yoon |
| 5,626,585 A | 5/1997 | Mittelstadt |
| 5,626,586 A | 5/1997 | Pistl et al. |
| 5,626,592 A | 5/1997 | Phillips |
| RE35,525 E | 6/1997 | Stefanchik et al. |
| 5,634,930 A | 6/1997 | Thornton et al. |
| 5,643,291 A | 7/1997 | Pier |
| 5,645,551 A | 7/1997 | Green |
| 5,645,553 A | 7/1997 | Kolesa |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier |
| 5,695,505 A | 12/1997 | Yoon |
| 5,697,938 A | 12/1997 | Jensen et al. |
| 5,700,270 A | 12/1997 | Peyser |
| 5,700,271 A | 12/1997 | Whitfield |
| 5,702,048 A | 12/1997 | Eberlin |
| 5,709,706 A | 1/1998 | Kienzle et al. |
| 5,713,911 A | 2/1998 | Racenet |
| 5,713,912 A | 2/1998 | Porter |
| 5,720,756 A | 2/1998 | Green |
| 5,722,982 A | 3/1998 | Ferreira et al. |
| 5,725,537 A | 3/1998 | Green |
| 5,725,538 A | 3/1998 | Green |
| 5,725,542 A | 3/1998 | Yoon |
| 5,733,295 A | 3/1998 | Back et al. |
| 5,755,726 A | 5/1998 | Pratt |
| 5,766,189 A | 6/1998 | Matsuno |
| 5,769,857 A | 6/1998 | Reztzov et al. |
| 5,772,673 A | 6/1998 | Cuny |
| 5,776,146 A | 7/1998 | Sackier et al. |
| 5,776,147 A * | 7/1998 | Dolendo .................. 606/142 |
| 5,779,718 A | 7/1998 | Green |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts |
| 5,792,150 A | 8/1998 | Pratt |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield |
| 5,833,700 A | 11/1998 | Fogelberg et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser |
| 5,868,761 A | 2/1999 | Nicholas |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi |
| 5,938,667 A | 8/1999 | Peyser |
| 5,951,574 A | 9/1999 | Stefanchik et al. |
| 5,972,003 A | 10/1999 | Rousseau |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| RE36,720 E | 5/2000 | Green |
| 6,059,799 A | 5/2000 | Aranyi |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis |
| 6,537,289 B1 * | 3/2003 | Kayan et al. .................. 606/158 |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 * | 8/2003 | Shipp .................. 606/143 |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 * | 1/2004 | Kayan et al. .................. 606/143 |
| 6,676,659 B2 | 1/2004 | Hutchins et al. |
| 6,679,894 B2 | 1/2004 | Damarati |
| RE38,445 E | 2/2004 | Pistl |
| 6,695,854 B1 | 2/2004 | Kayan |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 * | 8/2004 | Frantzen et al. .................. 606/151 |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |

(56) References Cited

U.S. PATENT DOCUMENTS

| | | | |
|---|---|---|---|
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,552,853 B2 * | 6/2009 | Mas et al. .................. 227/175.1 |
| 7,637,917 B2 | 12/2009 | Whitfield |
| 7,695,482 B2 | 4/2010 | Viola |
| 7,717,926 B2 | 5/2010 | Whitfield |
| 7,819,886 B2 | 10/2010 | Whitfield |
| 7,905,890 B2 | 3/2011 | Whitfield |
| 7,988,027 B2 | 8/2011 | Olson |
| 8,011,550 B2 | 9/2011 | Aranyi |
| 8,011,555 B2 | 9/2011 | Tarinelli |
| 8,016,178 B2 | 9/2011 | Olson |
| 8,021,375 B2 | 9/2011 | Aldrich |
| 8,021,378 B2 | 9/2011 | Sixto, Jr. |
| 8,056,565 B2 | 11/2011 | Zergiebel |
| 8,070,760 B2 | 12/2011 | Fujita |
| 8,083,668 B2 | 12/2011 | Durgin |
| 8,088,061 B2 | 1/2012 | Wells |
| 8,091,755 B2 | 1/2012 | Kayan |
| 8,097,004 B2 * | 1/2012 | Wild ............................ 606/142 |
| 8,128,643 B2 | 3/2012 | Aranyi |
| 8,142,451 B2 | 3/2012 | Boulnois |
| 8,157,149 B2 | 4/2012 | Olson |
| 8,157,151 B2 | 4/2012 | Ingmanson |
| 8,216,257 B2 | 7/2012 | Huitema |
| 8,236,012 B2 | 8/2012 | Molitor |
| 8,246,634 B2 | 8/2012 | Huitema |
| 8,246,635 B2 | 8/2012 | Huitema |
| 8,262,679 B2 | 9/2012 | Nguyen |
| 8,267,944 B2 | 9/2012 | Sorrentino |
| 8,267,945 B2 | 9/2012 | Nguyen |
| 8,267,946 B2 | 9/2012 | Whitfield |
| 8,282,655 B2 | 10/2012 | Whitfield |
| 8,328,822 B2 | 12/2012 | Huitema |
| 8,336,556 B2 | 12/2012 | Zergiebel |
| 8,348,130 B2 | 1/2013 | Shah |
| 8,357,171 B2 | 1/2013 | Whitfield |
| 8,371,491 B2 | 2/2013 | Huitema |
| 8,382,773 B2 | 2/2013 | Whitfield |
| 8,403,945 B2 | 3/2013 | Whitfield |
| 8,403,946 B2 | 3/2013 | Whitfield |
| 8,409,222 B2 | 4/2013 | Whitfield |
| 8,409,223 B2 | 4/2013 | Sorrentino |
| 8,419,752 B2 | 4/2013 | Sorrentino |
| 8,430,892 B2 | 4/2013 | Bindra |
| 8,444,660 B2 | 5/2013 | Adams |
| 8,465,502 B2 | 6/2013 | Zergiebel |
| 8,475,473 B2 | 7/2013 | Vandenbroek |
| 8,480,688 B2 | 7/2013 | Boulnois |
| 8,486,091 B2 | 7/2013 | Sorrentino |
| 8,491,608 B2 | 7/2013 | Sorrentino |
| 8,496,673 B2 | 7/2013 | Nguyen |
| 8,506,580 B2 | 8/2013 | Zergiebel |
| 8,512,357 B2 | 8/2013 | Viola |
| 8,523,882 B2 | 9/2013 | Huitema |
| 8,529,585 B2 | 9/2013 | Jacobs |
| 8,529,586 B2 | 9/2013 | Rosenberg |
| 8,529,588 B2 | 9/2013 | Ahlberg |
| 8,545,486 B2 | 10/2013 | Malkowski |
| 8,579,918 B2 | 11/2013 | Whitfield |
| 8,585,717 B2 | 11/2013 | Sorrentino |
| 8,603,109 B2 | 12/2013 | Aranyi |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |

(56) References Cited

U.S. PATENT DOCUMENTS

| | | |
|---|---|---|
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2004/0193213 A1 | 9/2004 | Aranyi |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1* | 9/2005 | Nakao ............ 606/142 |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1* | 10/2006 | Huitema et al. ............ 606/142 |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | A. Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |

(56) References Cited

U.S. PATENT DOCUMENTS

| | | | |
|---|---|---|---|
| 2008/0065118 A1 | 3/2008 | Damarati | |
| 2008/0065119 A1 | 3/2008 | Viola | |
| 2008/0243145 A1* | 10/2008 | Whitfield et al. | 606/143 |
| 2010/0010510 A1* | 1/2010 | Stefanchik | 606/142 |
| 2010/0057105 A1 | 3/2010 | Sorrentino | |
| 2010/0057107 A1 | 3/2010 | Sorrentino | |
| 2010/0274262 A1 | 10/2010 | Schulz et al. | |
| 2011/0087242 A1 | 4/2011 | Pribanic | |
| 2011/0137323 A1 | 6/2011 | Malkowski | |
| 2011/0208212 A1 | 8/2011 | Zergiebel | |
| 2011/0224701 A1 | 9/2011 | Menn | |
| 2011/0245847 A1 | 10/2011 | Menn | |
| 2012/0029534 A1 | 2/2012 | Whitfield | |
| 2012/0109158 A1 | 5/2012 | Zammataro | |
| 2012/0116420 A1 | 5/2012 | Sorrentino | |
| 2012/0123446 A1 | 5/2012 | Aranyi | |
| 2012/0197269 A1 | 8/2012 | Zammataro | |
| 2012/0265220 A1 | 10/2012 | Menn | |
| 2012/0277765 A1 | 11/2012 | Zammataro | |
| 2012/0330326 A1 | 12/2012 | Creston | |
| 2013/0110135 A1 | 5/2013 | Whitfield | |
| 2013/0131697 A1 | 5/2013 | Hartoumbekis | |
| 2013/0165952 A1 | 6/2013 | Whitfield | |
| 2013/0172910 A1 | 7/2013 | Malkowski | |
| 2013/0172911 A1 | 7/2013 | Rockrohr | |
| 2013/0172912 A1 | 7/2013 | Whitfield | |
| 2013/0190779 A1 | 7/2013 | Whitfield | |
| 2013/0190780 A1 | 7/2013 | Whitfield | |
| 2013/0274767 A1 | 10/2013 | Sorrentino | |
| 2013/0289583 A1 | 10/2013 | Zergiebel | |
| 2013/0296891 A1 | 11/2013 | Hartoumbekis | |
| 2013/0296892 A1 | 11/2013 | Sorrentino | |
| 2013/0310849 A1 | 11/2013 | Malkowski | |

FOREIGN PATENT DOCUMENTS

| | | |
|---|---|---|
| EP | 0 086 721 | 8/1983 |
| EP | 0 089 737 A1 | 9/1983 |
| EP | 0 324 166 A2 | 7/1989 |
| EP | 0 392 750 A1 | 10/1990 |
| EP | 0 409 569 A1 | 1/1991 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0 755 655 A2 | 1/1997 |
| EP | 0 769 274 | 4/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 187 | 10/2006 |
| EP | 1 712 191 A2 | 10/2006 |
| EP | 1 757 236 | 2/2007 |
| EP | 1 813 199 A1 | 8/2007 |
| EP | 1 908 423 | 4/2008 |
| EP | 1 908 423 A2 | 4/2008 |
| EP | 1 913 881 A1 | 4/2008 |
| EP | 2 229 895 A1 | 9/2010 |
| EP | 2 332 471 | 6/2011 |
| JP | 2003 033361 A | 2/2003 |
| WO | WO 03/086207 | 10/2003 |
| WO | WO 03/092473 | 11/2003 |
| WO | WO 2005/091457 A1 | 9/2005 |
| WO | WO 2006/042076 | 4/2006 |
| WO | WO 2006/042076 A2 | 4/2006 |
| WO | WO 2006/042084 A2 | 4/2006 |
| WO | WO 2006/042110 | 4/2006 |
| WO | WO 2006/042110 A2 | 4/2006 |
| WO | WO 2006/042141 | 4/2006 |
| WO | WO 2006/135479 | 12/2006 |
| WO | WO 2008/118928 | 10/2008 |
| WO | WO 2008/118928 A2 | 10/2008 |
| WO | WO 2008/127968 | 10/2008 |
| WO | WO 2008/127968 A2 | 10/2008 |

OTHER PUBLICATIONS

European Search Report corresponding to EP 05810218.7, mailed on May 20, 2011; completed on Apr. 18, 2011; 3 pages.

European Search Report corresponding to EP 05807612.6, mailed on May 20, 2011; completed on May 2, 2011; 3 pages.

Extended European Search Report corresponding to EP 10251737.2, mailed on May 20, 2011; completed on May 9, 2011; 4 pages.

The extended European Search Report corresponding to European Application No. EP 12 16 2288.0, completed Jun. 4, 2012 and mailed Jul. 7, 2012; (6 Pages).

The extended European Search Report corresponding to European Application No. EP 12 16 5891.8, completed Jun. 12, 2012 and mailed Jun. 20, 2012; (6 Pages).

The extended European Search Report corresponding to European Application No. EP 12 16 4955.2, completed Aug. 23, 2012 and mailed Sep. 4, 2012; (5 Pages).

The extended International Search Report corresponding to European Application No. 07 25 3905.9, completed Jan. 29, 2008; mailed Feb. 7, 2008; (7 Pages).

The partial International Search Report corresponding to European Application No. EP 07 25 3807.7, completed Jul. 23, 2008: mailed Aug. 1, 2008; (3 pages).

International Search Report corresponding to International Application No. PCT/US08/58185, completed Sep. 4, 2008; mailed Sep. 9, 2008; (2 Pages).

International Search Report corresponding to International Application No. PCT/US08/59859, completed Sep. 14, 2008, mailed Sep. 18, 2008; (2 Pages).

The Extended European Search Report corresponding to European Application No. 07 25 3807.7, completed Nov. 7, 2008; mailed Nov. 26, 2008; (11 Pages).

The extended European Search Report corresponding to European Application No. EP 09252049.3, completed Dec. 11, 2009; mailed Jan. 12, 2010; (3 Pages).

The Extended European Search Report corresponding to European Application No. EP 09252050.1, completed Dec. 23, 2009; mailed Jan. 21, 2010; (3 Pages).

The extended European Search Report corresponding to European Application No. EP 09252031.9, completed Dec. 21, 2009; mailed Jan. 28, 2010; (3 Pages).

The extended European Search Report corresponding to European Application No. EP 09252052.7, completed Nov. 16, 2009; mailed Nov. 24, 2009; (3 Pages).

The extended European Search Report corresponding to European Application No. EP 09252053.5, completed Nov. 24, 2009; mailed Dec. 1, 2009; (3 Pages).

The extended European Search Report corresponding to European Application No. EP 09252054.3, completed Jan. 7, 2010; mailed Jan. 22, 2010; (3 Pages).

Extended European Search Report corresponding to European Application No. 09252056.8, completed Jan. 8, 2010; mailed Feb. 5, 2010; (3 Pages).

Extended European Search Report corresponding to European Application No. EP 10250497.4, completed May 4, 2010; mailed May 12, 2010; (6 Pages).

"Salute II Disposable Fixation Device", Technique Guide—Laparoscopic and Open Inguinal and Ventral Hernia Repair; Davol, A Bard Company, 2006; (7 Pages).

European Search Report corresponding to European Application No. EP 05 80 2686.5, completed Jan. 9, 2012; mailed Jan. 18, 2012; (3 Pages).

The extended European Search Report corresponding to European Application No. EP 12 15 1313.9, completed Mar. 20, 2012 and mailed Apr. 12, 2012; (5 Pages).

The extended European Search Report corresponding to European Application No. EP 12 16 1291.5, completed Apr. 24, 2012 and mailed May 4, 2012; (5 Pages).

(56) References Cited

OTHER PUBLICATIONS

The extended European Search Report corresponding to European Application No. EP 12 18 6401.1, completed Nov. 22, 2012 and mailed Nov. 30, 2012; (7 Pages).
The extended European Search Report corresponding to European Application No. EP 12 18 6448.2, completed Nov. 28, 2012 and mailed Dec. 10, 2012; (6 Pages).
The extended European Search Report corresponding to European Application No. EP 12 19 1706.6, completed Dec. 19, 2012 and mailed Jan. 8, 2013; (6 Pages).
The extended European Search Report corresponding to European Application No. EP 11 25 0754.6, completed Oct. 22, 2012 and mailed Oct. 31, 2012; (6 Pages).
The extended European Search Report corresponding to European Application No. EP 11250214.1, completed May 25, 2011; mailed Jun. 1, 2011; (3 Pages).
Extended European Search Report corresponding to EP 12 19 8745.7, completed Mar. 19, 2013 and mailed Apr. 11, 2013; (8 pp).
Extended European Search Report corresponding to EP 12 15 2989.5, completed Apr. 9, 2013 and mailed Apr. 18, 2013; (9 pp).
Extended European Search Report corresponding to EP 08 73 2820,9, completed Jul. 2, 2013 and mailed Jul. 9, 2013; (10 pp).
Extended European Search Report corresponding to EP 12 19 1706.6, completed Dec. 19, 2012 and mailed Jan. 8, 2013; (6 pp).
Extended European Search Report corresponding to EP 13 172008.8, completed Aug. 14, 2013 and mailed Aug. 28, 2013; (8 pp).

\* cited by examiner

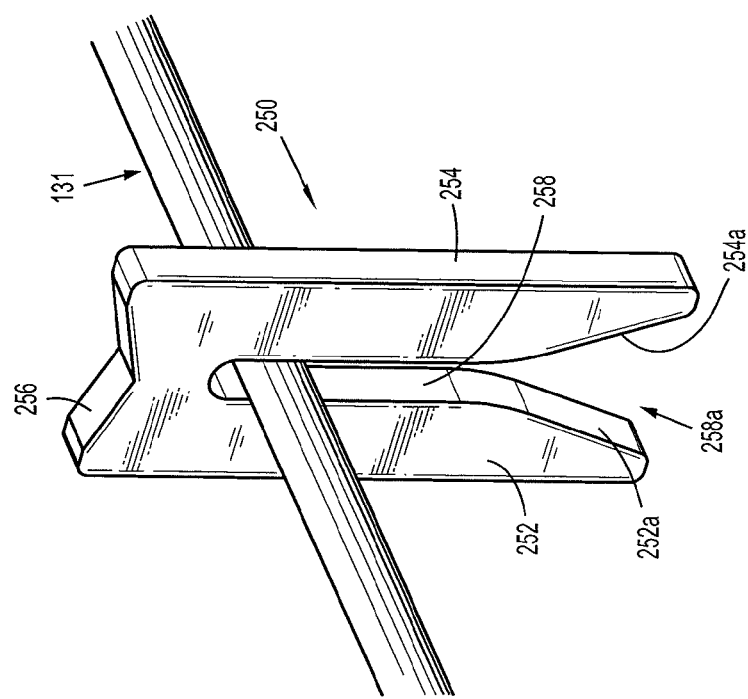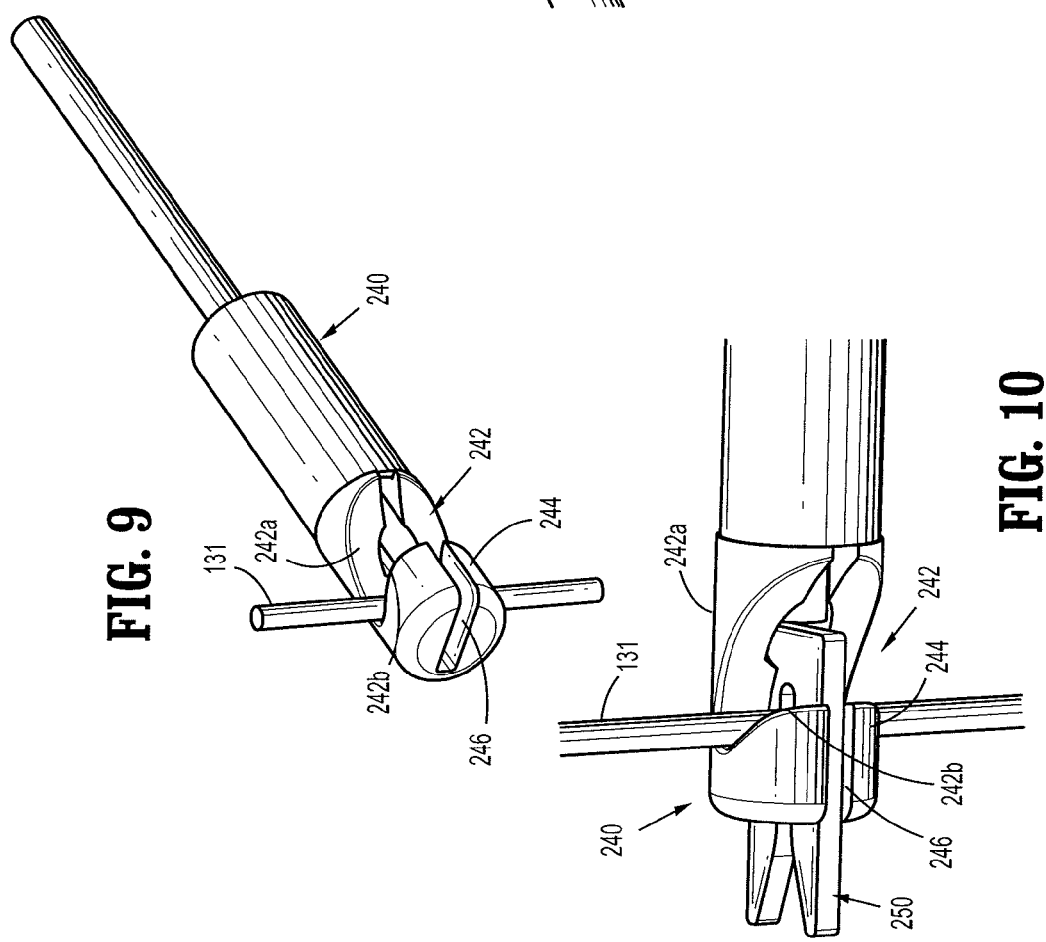

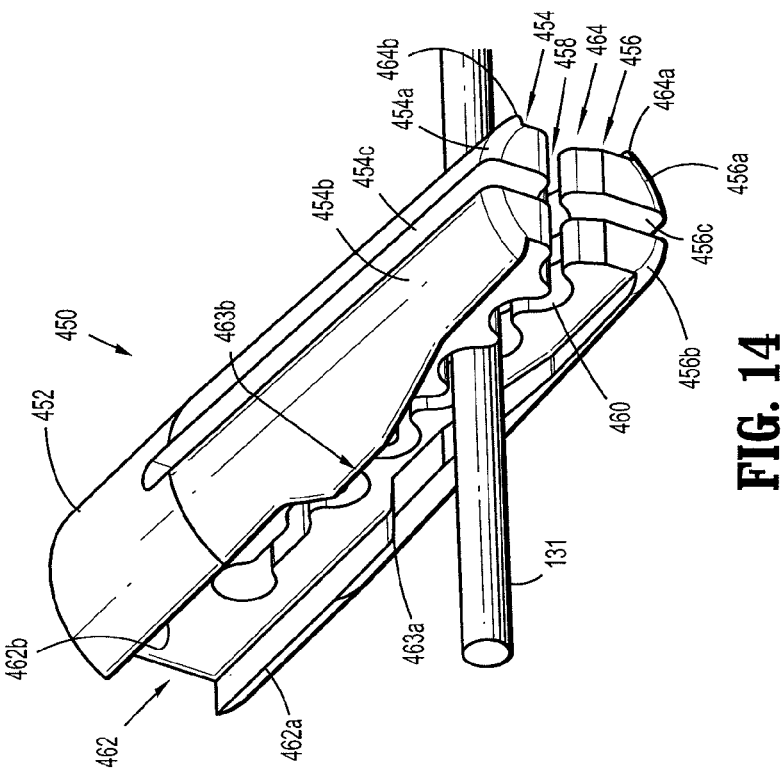
FIG. 14
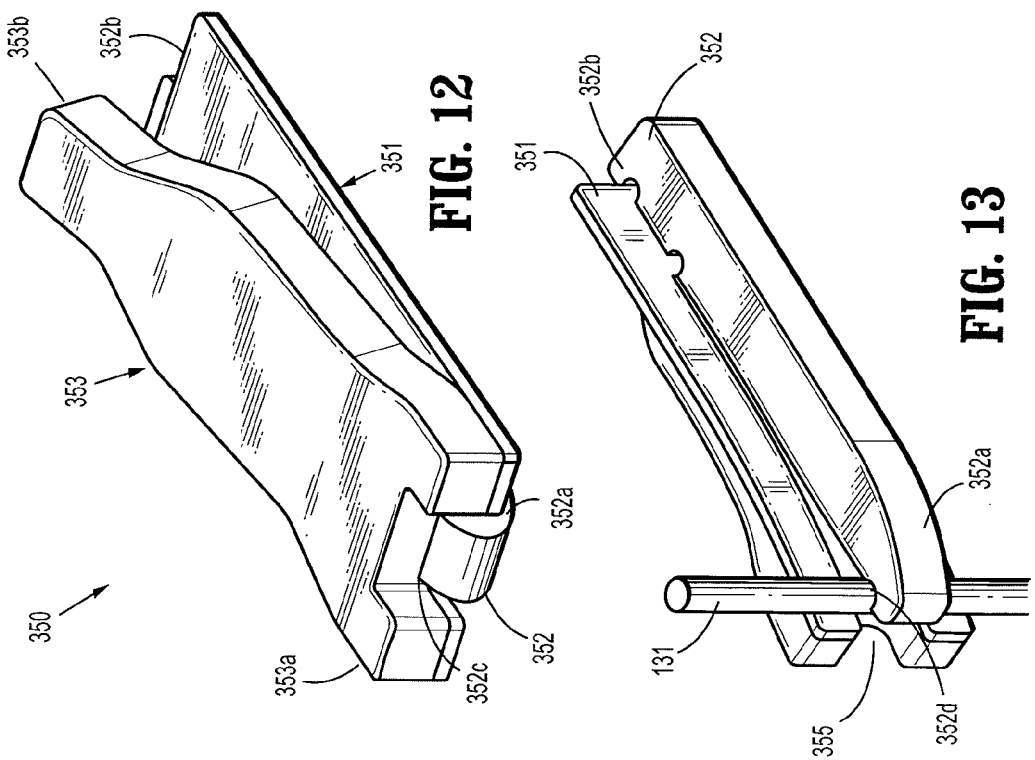
FIG. 12
FIG. 13

SUTURE CLIP APPLIER

CROSS-REFERENCE TO RELATED APPLICATIONS

The present application claims the benefit of and priority to U.S. Provisional Application Ser. No. 61/250,894, filed on Oct. 13, 2009, the entire content of which is incorporated herein by reference.

BACKGROUND

1. Technical Field

The present disclosure relates to a device for use in a surgical procedure. More particularly, the present disclosure relates to a surgical suture clip applier adapted for securing sutures during an endoscopic or laparoscopic procedure.

2. Background of Related Art

In surgical operations it is well known that surgical sutures are applied to repair the body tissue. Such sutures generally are of the non-absorbable or the absorbable type and are generally applied with the use of surgical needles. If the sutures are non-absorbable, they may or may not be removed after an estimated predetermined healing period has passed. Absorbable sutures are absorbed gradually over time by coming in contact with moisture in the human body.

In many surgical procedures, application of sutures generally involves knotting or tying the suture after it is applied to the body tissue in order to retain its position with respect to the tissue and to maintain the tissue in the repaired position. In cases where the surgeon has full access to the operative site by virtue of a large incision, knotting the suture or applying knotting or equivalent devices is relatively simple due to the access provided by the incision.

In endoscopic and laparoscopic procedures, on the other hand, large incisions are avoided. In laparoscopic procedures surgery is performed in the interior of the abdomen through a small incision; in endoscopic procedures surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that instruments to be used in such procedures generally be both long and narrow.

In laparoscopic and endoscopic procedures surgical sutures are generally applied by directing and manipulating needled sutures through an aperture in the body or through elongated narrow tubes known as cannulae with the assistance of specially designed needle graspers, needle drivers, and the like. However, tying the sutures in such procedures can be relatively difficult due to the limited access afforded to the surgeon through the narrow tubes. In particular, since biocompatible, preferably bioabsorbable, sutures are generally used in such procedures it would be desirable to have available a cinching device and system that facilitates tying the sutures through the tubes in a manner to retain their position in the body tissue at least until the healing process is in full progress. The use of the term "endoscopic" herein contemplates endoscopic as well as laparoscopic procedures.

SUMMARY

The present disclosure relates to surgical suture clip appliers, suture clips and methods of their use for securing sutures during an endoscopic or laparoscopic procedure.

According to an aspect of the present disclosure, a suture clip applier is provided and includes a housing; an elongated plunger slidably supported in the housing, the plunger having a distal end portion disposed within the housing and a proximal end portion extending from a proximal end of the housing; a hollow tube extending distally from the housing and defining a lumen therethrough; an actuation member having a distal end extending into the hollow tube and a proximal end operatively engaged with the plunger; and a working tip coupled to a distal end of the hollow tube. The working tip has a substantially U-shaped transverse cross-sectional profile defining a channel having a base wall and a pair of spaced apart side walls. The working tip defines a lower contact surface along an internal face of the base wall, and an upper contact surface defined along an upper end surface of each side wall. The upper contact surface of each side wall includes a distal recess formed near a distal end of thereof and a proximal recess formed proximal of the distal recess; and an internal retaining surface on both side walls parallel to the base wall. In use, the distal end of the actuation member is configured to engage a suture clip loaded into the working tip.

The plunger may define a race formed in a surface thereof. The race may include a plurality of portions each defining a cam surface of varying depth. The clip applier may include a rocker arm having a distal end portion and proximal end portion. The rocker arm may have a follower pin extending therefrom near the distal end portion thereof and a retaining pin near the proximal end portion thereof. The rocker arm may be pivotally attached to the housing by the retaining pin and the follower pin may be slidably disposed within the race of the plunger to modulate the motion of the plunger and actuation member.

The race may define four interconnected cam portions, with each cam portion having a start position and an end position, and each cam is deepest at its respective start position and shallowest at its respective end position.

The rocker arm may be elastically deformable laterally from the plunger thereby providing a biasing force upon the follower pin and plunger relative to the body.

The clip applier may further include finger loops extending from the housing.

The actuation member may be configured to transmit axial translative forces to the suture clip.

The clip applier may further include a biasing member disposed within the housing and providing a proximal bias upon the plunger relative to the housing. The biasing member may be a coil spring.

The distal recess and the proximal recess, formed in each vertical side wall, may be interconnected by a camming surface.

According to another aspect of the present disclosure, a suture clip for selective attachment to a suture is provided and includes an elongated flexible beam having a distal end portion, a proximal end portion, a top surface and a bottom surface, the flexible beam further including a pair of arms extending laterally therefrom; and an elongated rigid channel, wherein the elongated rigid channel has a substantially U-shaped transverse cross-sectional profile with a horizontal base wall and vertical side walls having a distal end portion and proximal end portion, wherein each vertical side wall defines a holding step formed in an upper edge thereof. The flexible beam and the channel are coupled to one another at their proximal end portions; and the pair of arms of the flexible beam are in registration with a corresponding holding step framed in the upper edge of the vertical side walls.

A proximal end portion of the pair of vertical side walls of the channel of the suture clip may include inwardly projecting lips for retaining the proximal end portion of the beam within the channel. The proximal end portions of the beam and channel may be adhesively coupled to one another.

The pair of arms of the flexible beam may project beyond the pair of vertical side walls of the channel.

According to a further aspect of the present disclosure, a suture clip applier system is provided and includes a suture clip applier for filing a suture clip onto a suture. The clip applier includes a housing; an elongated plunger slidably supported in the housing, the plunger having a distal end portion disposed within the housing and a proximal end portion extending from a proximal end of the housing; a hollow tube extending distally from the housing and defining a lumen therethrough; an actuation member having a distal end extending into the hollow tube and a proximal end operatively engaged with the plunger; and a working tip coupled to a distal end of the hollow tube. The working tip has a substantially U-shaped transverse cross-sectional profile defining a channel having a base wall and a pair of spaced apart side walls. The working tip defines a lower contact surface along an internal face of the base wall, and an upper contact surface defined along an upper end surface of each side wall. The upper contact surface of each side wall includes a distal recess formed near a distal end thereof and a proximal recess formed proximal of the distal recess; and an internal retaining surface on both side walls parallel to the base wall. The distal end of the actuation member is configured to engage a suture clip loaded into the working tip The suture clip applier system further includes a suture clip loadable into and deployable from the working tip. The suture clip includes an elongated flexible beam having a distal end portion, a proximal end portion, a top surface and a bottom surface, the flexible beam further including a pair of arms extending laterally therefrom; and an elongated rigid channel, wherein the elongated rigid channel has a substantially U-shaped transverse cross-sectional profile with a horizontal base wall and vertical side walls having a distal end portion and proximal end portion, wherein each vertical side wall defines a holding step formed in an upper edge thereof. The flexible beam and the channel are coupled to one another at their proximal end portions. The pair of arms of the flexible beam are in registration with a corresponding holding step formed in the upper edge of the vertical side walls; and, in use, as the suture clip is urged in a distal direction relative to the working tip, the flexible beam is splayed apart from the channel to open the suture clip for receipt of a suture therein.

The plunger of the clip applier defines a race formed in a surface thereof, the race includes a plurality of portions each defining a cam surface of varying depth; and the clip applier includes a rocker arm having a distal end portion and proximal end portion, the rocker arm has a follower pin extending therefrom near the distal end portion thereof and a retaining pin near the proximal end portion thereof. The rocker arm is pivotally attached to the housing by the retaining pin and the follower pin is slidably disposed with in the race of the plunger to modulate the motion of the plunger and actuation member.

The race may define four interconnected cam portion, with each cam portion having a start position and an end position and each cam is deepest at its respective start position and shallowest at its respective end position.

The rocker arm of the clip applier may be elastically deformable laterally from the plunger thereby providing a biasing force upon the follower pin and plunger relative to the body.

The clip applier may further include a biasing member disposed within the housing and providing a proximal bias upon the plunger relative to the housing. The distal recess and the proximal recess formed in each vertical side wall may be interconnected by a camming surface.

A proximal end portion of the pair of vertical sides walls of the channel of the suture clip may include inwardly projecting lips for retaining the proximal end portion of the beam within the channel. The pair of arms of the suture clip may project beyond the pair of vertical side walls of the channel thereof.

According to yet another aspect of the present disclosure, a method of securing a suture through an incision is provided. The method includes the steps of providing a suture clip applier having a working tip configured to retain and fire a suture clip; providing a suture clip having a biased closed configuration; loading the suture clip into the working tip of the clip applier; translating the suture clip distally relative to the working tip to a first position wherein the suture clip is splayed open; inserting a suture into the opened suture clip; and translating the suture clip distally relative to the working tip such that the suture clip is ejected from the working tip and biased to the closed configuration to close on and to retain the suture.

According to still another embodiment of the present disclosure, a method of securing a suture through an incision is provided and includes the steps of providing a suture clip applier having a working tip, and providing a suture clip. The working tip of the suture clip has a substantially U-shaped transverse cross-sectional profile defining a channel having a base wall and a pair of spaced apart side walls. The working tip defines a lower contact surface along an internal face of the base wall; and an upper contact surface defined along an upper end surface of each side wall. The upper contact surface of each side wall includes a distal recess formed near a distal end of thereof and a proximal recess formed proximal of the distal recess; and an internal retaining surface projecting inwardly from both side walls of the channel. The suture clip includes an elongated flexible beam having a distal end portion, a proximal end portion, a top surface and a bottom surface, the flexible beam further including a pair of aims extending laterally therefrom; and an elongated rigid channel. The elongated rigid channel of the suture clip has a substantially U-shaped transverse cross-sectional profile with a horizontal base wall and a pair of spaced apart vertical side walls having a distal end portion and a proximal end portion. Each vertical side wall of the suture clip defines a holding step formed in an upper edge thereof. The flexible beam and the channel of the clip are coupled to one another at their proximal end portions; and the pair of arms of the flexible beam are in registration with a corresponding holding step formed in the upper edge of the vertical side walls of the channel of the clip.

The method further includes the steps of loading a suture clip into the working tip such that the vertical side walls of the clip channel abut the retaining surface of the working tip, and the laterally extending arms of the flexible beam rest in the proximal recess of the working tip; and translating the suture clip distally relative to the working tip such that the laterally extending arms of the suture clip are translated from the proximal recess of the working tip channel to the distal recess of the working tip while the clip channel is retained by the internal retaining surfaces of the working tip such that the distal ends of the flexible beam and the channel of the suture clip are separated to define an opening, and so that the distal end of the suture clip protrudes from the working tip.

The method further includes the steps of inserting a suture into the opening of the suture clip; and translating the suture clip distally relative to the working tip such that the suture clip is ejected from the working tip and the flexible beam and the channel of the clip are biased toward one another to close on and retain the suture.

BRIEF DESCRIPTION OF THE DRAWINGS

The present disclosure will be more fully appreciated as the same becomes better understood from the following detailed description when considered in connection with the following drawings, in which:

FIG. 9 is a perspective view of a clip applier according to another embodiment of the present disclosure including a hook-shaped working tip for use with a flat suture clip;

FIG. 10 is a perspective view of the hook-shaped working tip illustrating an attachment of the suture clip to a suture;

FIG. 11 is a perspective view of the suture clip shown secured upon a suture;

FIG. 12 is a perspective view of another embodiment of a spring clip according to the present disclosure and shown in its neutral position;

FIG. 13 is a perspective view of the suture clip of FIG. 12 shown on a suture; and FIG. 14 is a perspective view of a suture clip according to yet another embodiment of the present disclosure.

DETAILED DESCRIPTION OF THE EMBODIMENTS

Figure 1:
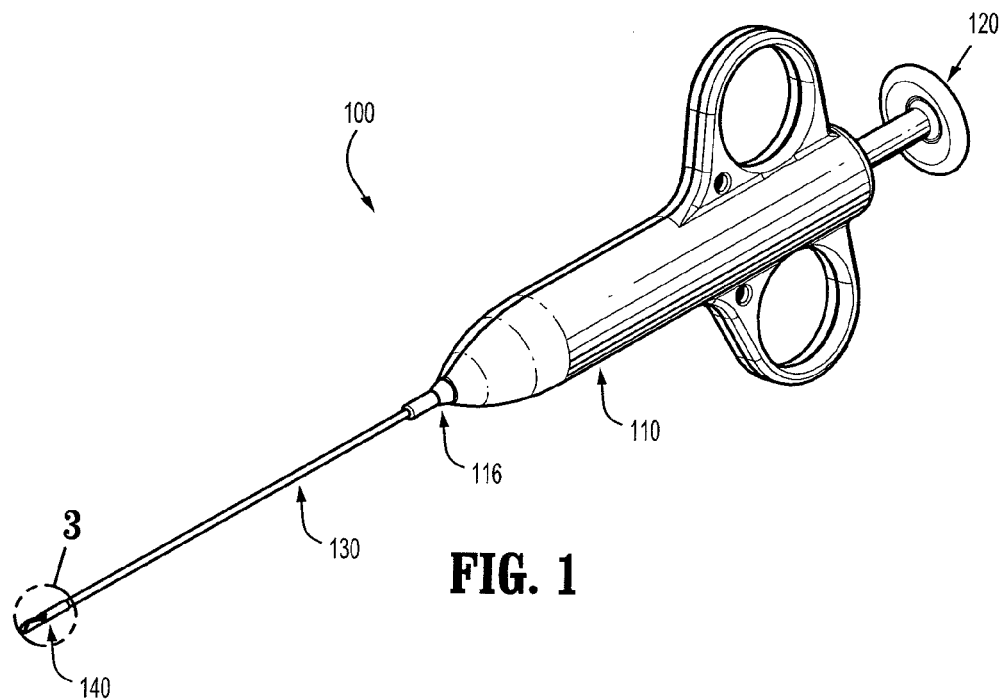
FIG. 1 is a perspective view of a clip applier according to an embodiment of the present disclosure.

While embodiments of the present disclosure are susceptible to various modifications and alternative constructions, certain illustrated embodiments thereof have been shown in the drawings and will be described below in detail. It should be understood, however, that there is no intention to limit the embodiments of the present disclosure to the specific form disclosed, but, on the contrary, the embodiments are intended to cover all modifications, alternative constructions, and equivalents falling within the spirit and scope of the present disclosure as defined in the claims.

While various embodiments of the invention are described herein, it is to be distinctly understood that this invention is not limited thereto but may be variously embodied to practice within the scope of the following claims. The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

The present disclosure relates to devices and methods for applying suture clips in an endoscopic, endoluminal, laparoscopic, or other surgical setting. Throughout the following description, the term "proximal," will refer to the end of a device or system that is closest to the operator, while the term "distal" will refer to the end of the device or system that is farthest from the operator.

With reference to FIGS. 1-7B, a clip applier, in accordance with the present disclosure, is generally designated as 100. Clip applier 100 includes a body or housing 110, a plunger 120 disposed substantially within body 110, a hollow outer tube 160 extending from and operatively supported by body 110, a working tip 140 supported on at a distal end of outer tube 160 and configured for operation on or with a suture clip 150, and an actuation member 130 extending through body 110 and hollow outer tube 160 and coupled at a proximal end thereof to plunger 120.

Figure 2:
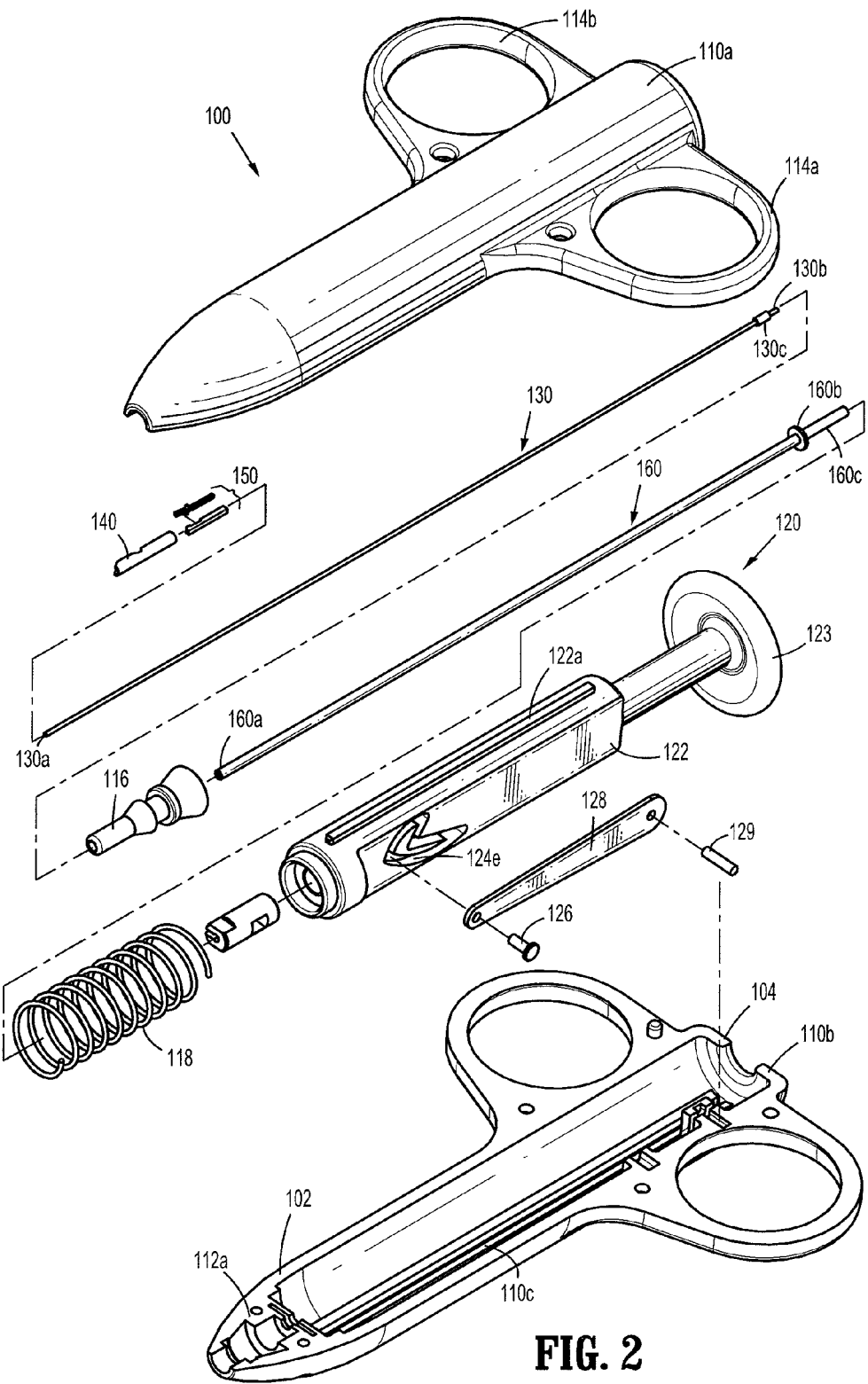
FIG. 2 is a perspective view, with the parts separated, of the clip applier of FIG. 1.
Figure 2A:
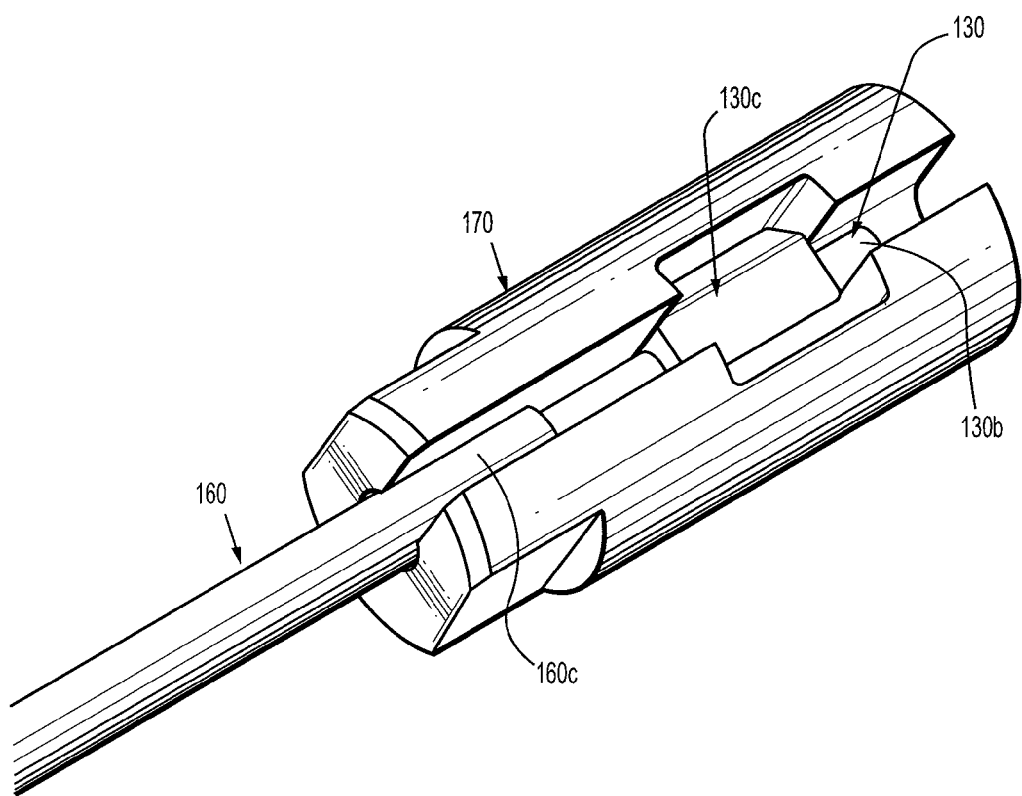
FIG. 2A is an enlarged perspective view illustrating the connection of a crimp of an actuating member in a set screw.
Figure 4:
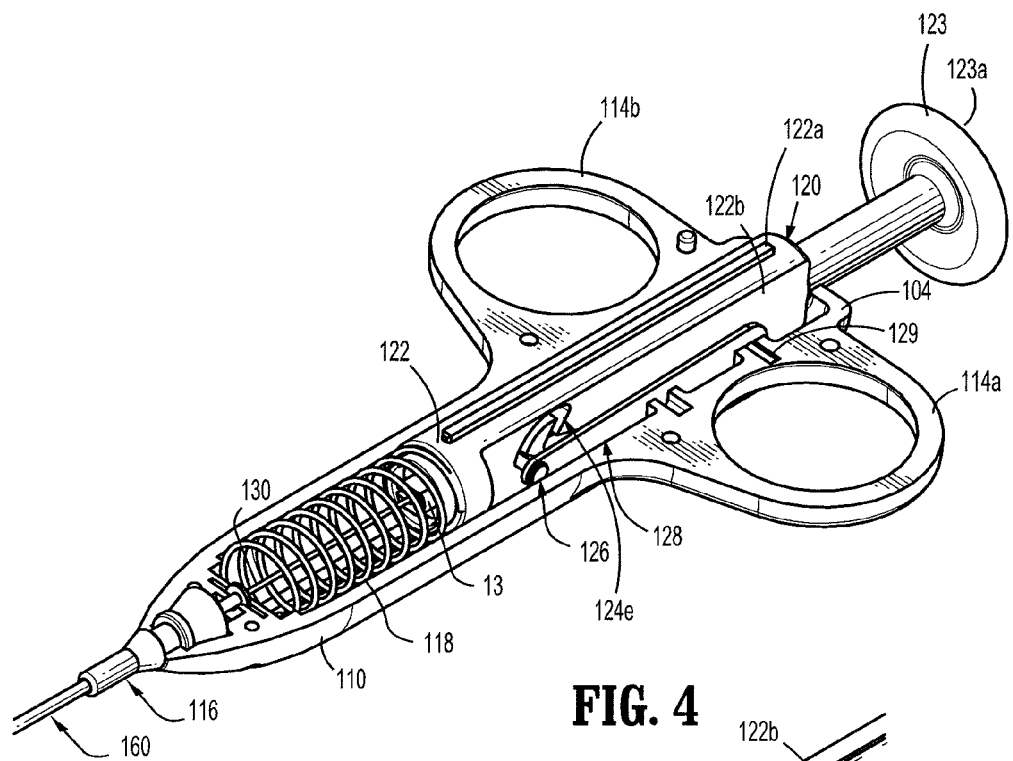
FIG. 4 is a perspective cut-away view of the clip applier of FIG. 1, illustrated with a body half-section removed therefrom.

With reference to FIGS. 1, 2 and 4, body 110 is a hollow, elongated, annular member with a distal end portion 102 and proximal end portion 104 defining a longitudinal axis. The distal end portion 102 of body 110 has a frustoconical profile which narrows to define a distal opening 112a which is coincident with the exterior circumference of and supports a proximal end 160b of outer tube 160. As seen in FIG. 2, body 110 may be formed in a pair of half-sections 110a, 110b that are joined to one another using know techniques in the art, such as, for example, gluing, welding, fastening and the like.

As shown in FIGS. 1 and 2, it is contemplated that a substantially frustoconical, hollow strain relief 116, substantially composed of a complaint material, is disposed or supported at a distal end portion 102 of body 110. Strain relief 116 is configured to permit outer tube 160 to pass therethrough in order to provide a bias to outer tube 160 in order to help maintain outer tube in substantially parallel relation with the longitudinal axis.

With further reference to FIGS. 1, 2 and 4, a proximal end portion 104 of body 110 further includes opposing co-planar annular projections defining finger engaging loops 114a, 114b.

With reference to FIG. 4, plunger 120 is an elongated substantially cylindrical member defining a distal body portion 122 disposed within body 110 and a proximal end portion 123 projecting from the proximal end portion 104 of body 110. Distal body portion 122 of plunger 120 has a pair of opposed, protruding, longitudinally extending rails 122a (see FIG. 5) configured to be slidably retained within a complementary recess 110c (only one recess shown in FIG. 2) formed in an internal face of body half 110b of body 110 so as to facilitate linear translation along the longitudinal axis of body 110.

Proximal end portion 123 of plunger 120 protrudes from body 110. Proximal end portion 123 of plunger 120, which protrudes from body 110, defines an actuation portion 123a which may be configured to be actuated by an operator's thumb, linear actuator, or other linear motion device known in the art.

Clip applier 100 includes a biasing member 118 disposed within body 110 and retained between the distal end of plunger 120 and an internal distal surface of body 110. Biasing member 118 may be an elastically deformable helical coil which provides a biasing force upon plunger 120 relative to body 110.

Figure 5:
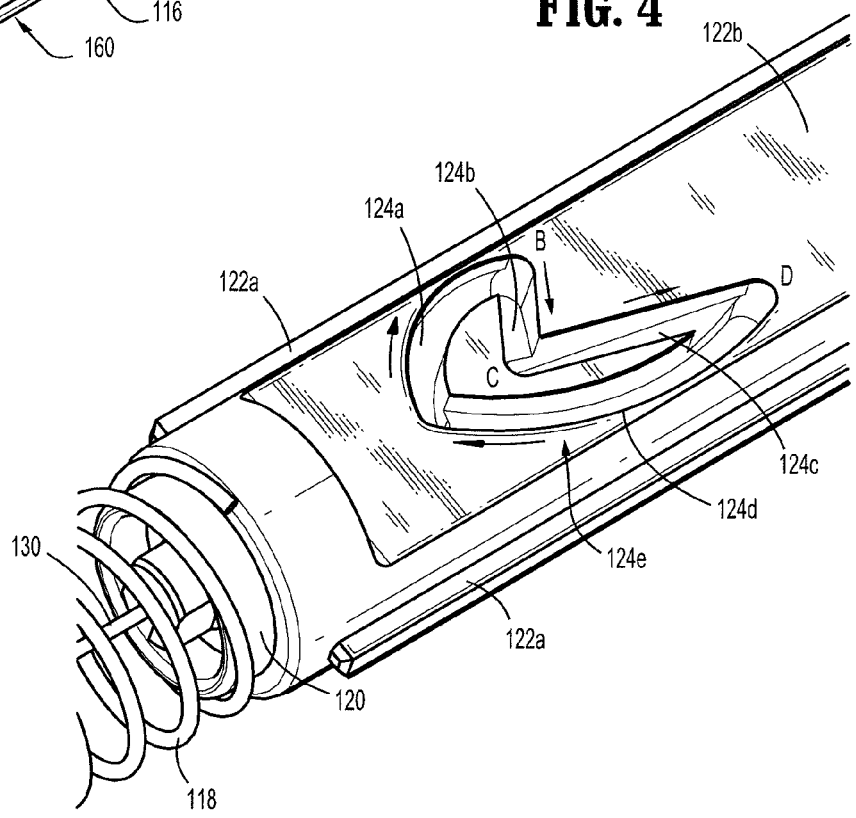
FIG. 5 is an enlarged view of the proximal end portion of the suture clip applier of FIG. 3.

With reference to FIGS. 4 and 5, one or more sides of distal body portion 122 of plunger 120 are flattened to define a surface 122b. Further, distal body portion 122 includes an audible/tactile feedback member defined by a race 124e formed in surface 122b of distal body portion 122. Race 124e includes a series of cam channels 124a-124d, each defining stepped or sloping cam surfaces 125a-125d. The depth of cam channels 124a-124d is such that they are deepest at the furthest counter-clockwise point along their respective paths. Race 124e accommodates a follower pin 126 that is coupled to and projects traversely from an end of a rocker arm 128 which is itself pivotally connected to body 110 by a proximal pin 129. Rocker arm 128 may be in the form of a biasing member, such as a leaf spring, to thereby exert a force upon follower pin 126 relative to body 110 so as to bias follower pin 126 against sloping cam surfaces 125a-125d of race 124e which provides control of the plunger stop positions as further detailed below.

The motion of plunger 120, actuating member 130 and clip 150 are modulated by the travel of follower pin 126 through race 124e. Plunger 120, actuating member 130, and clip 150 cannot be displaced until the proximal end portion 123 of plunger 120 is translated distally relative to body 110 by the operator, with sufficient force to overcome the biasing forces of biasing member 118 and rocker arm 128 and displace follower pin 126 along cam surfaces 125a-125d of race 124e. When plunger 120 is so actuated, follower pin 126 is caused to travel clockwise through the aforementioned cams. As follower pin 126 translates along a particular cam channel 124a-124d, respective cam surface 125a-125d urges follower pin 126 out of race 124e and exerts a biasing force on rocker arm 128. As follower pin 126 passes from one cam channel 124a-124d to an adjacent cam channel 124a-124d, across the step defined between adjacent cam surfaces 125a-125d, the bias force of the rockers arm 128 drive follower pin 126 against a cam surface 125a-125d, thereby creating an audible/tactile indication to the user. An audible/tactile indication may be provided for each stage of the firing sequence.

With reference to FIGS. 1 and 2, outer tube 160 of clip applier 100 is a hollow elongated tubular member including a distal end portion 160a, a proximal end portion 160b, and a lumen extending therethrough. Actuation member 130 is slidably disposed at least partially within the lumen of outer tube 160. It is contemplated that outer tube 160 may be rigid or flexible. It is further contemplated that outer tube 160 is a hollow tube with a substantially elliptical or rectilinear traverse cross-sectional profile.

With continued reference to FIGS. 1 and 2, actuation member 130 of clip applier 100 is a solid shaft like member including a distal end portion 130a and a proximal end portion 130b. As mentioned above, distal end portion 130a of actuation member 130 extends through the lumen of outer tube 160, and proximal end portion 130b of actuation member 130 is connected or secured to distal body portion 122 of plunger 120.

As seen in FIGS. 2, 2A, 4 and 5, clip applier includes a set screw 170 disposed in plunger 120 and secured to actuation member 130. In particular, set screw 170 defines a shaped cavity 170a configured to receive a stop or crimp 130c affixed to proximal end 130b of actuation member 130, whereby set screw 170 is axially and rotatably fixed with respect to actuation member 130. Additionally, a proximal end 160c of outer tube 160 is received and secured within a distal end of set screw 170. It is contemplated that proximal end 160c of outer tube 160 is threadably connected to set screw 170. In this manner, as set screw 170 is rotated with respected to outer tube 160, outer tube 160 is axially displaced relative to actuation member 130. In this manner, set screw 170 functions to enable fine tuning of the position of a distal tip or distal end portion 130a of actuation member 130 relative to distal end 160a of outer tube 160.

Figure 3:
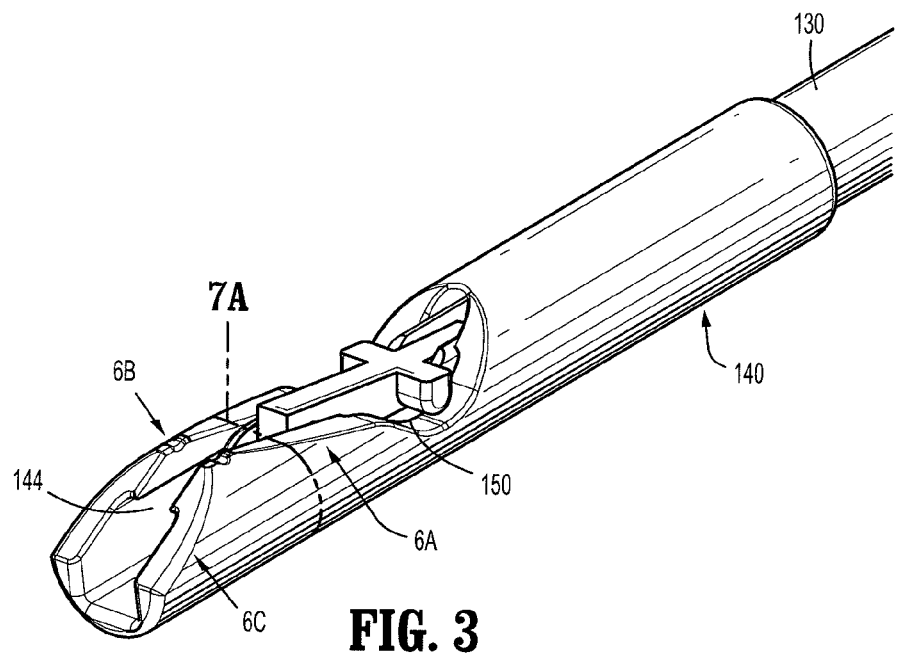
FIG. 3 is an enlarged perspective view of the indicated area of detail of FIG. 1, illustrating a clip loaded in a distal end of the clip applier.
Figure 7A:
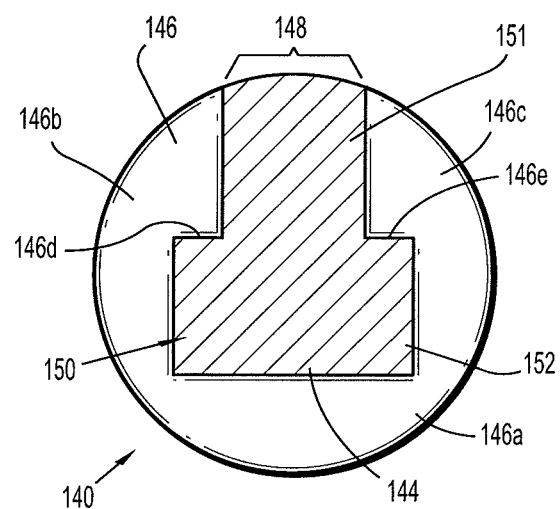
FIG. 7A is an enlarged cross-sectional view of the working tip and clip according to section A of FIG. 2.

With reference to FIGS. 3 and 7A, working tip 140 of clip applier 100 is operatively supported at its proximal end portion 140a to a distal end 160a of outer hollow tube 160. Working tip 140 has a substantially centrally disposed lumen 144 having a transverse cross-sectional profile, at the distal end of working tip 140, that is configured to retain clip 150. The shape of working tip 140 is described in greater detail hereinbelow.

Figure 7B:
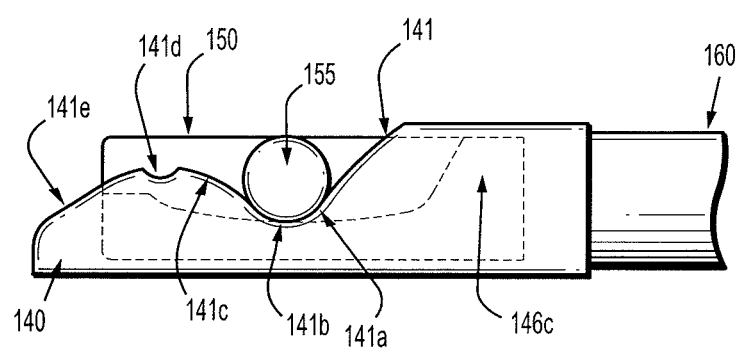
FIG. 7B is a side view of the working tip and clip of FIG. 2.

With reference to FIGS. 3, 7A and 7B, lumen 144 of working tip 140 is enclosed near a proximal end portion 140b thereof. Meanwhile, a distal end portion 140a of working tip 140 has been cut away to reveal or expose lumen 144, thereby defining a channel 146 having a pair of contact or cam surfaces 141 along which a cross beam 155 of suture clip 150 can travel, as will be described in greater detail below.

With reference to FIG. 7A, channel 146 of working tip 140 includes a base wall 146a and a pair of upstanding side walls 146b, 146c. Each side wall 146b, 146c defines a respective ledge 146d, 146e, extending into lumen 146 and extending substantially along the length of working tip 140.

With reference to FIG. 7B, upstanding side walls 146b, 146c have material removed therefrom defining a cam surface 141 along which traverse cross beams 155 of clip 150 can travel. Cam surface 141 includes, beginning with the proximal-most portion of the cam surface 141, a proximal shoulder 141a, a proximal retaining groove 141b, a medial incline 141c, a distal retaining groove 141d, and a distal ejection shoulder 141e.

Figure 6:
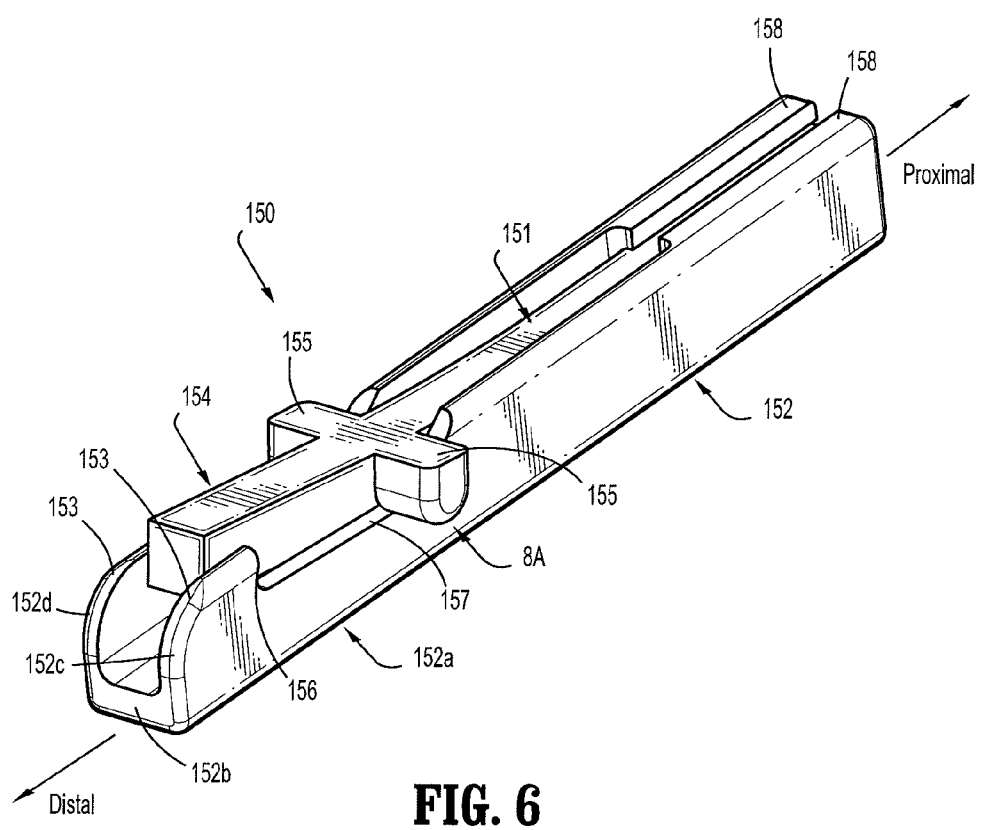
FIG. 6 is an enlarged perspective view of a suture clip according to an embodiment of the present disclosure, for use in the clip applier of FIGS. 1-5.

As shown in FIG. 6, a suture clip 150, according to the present disclosure, includes a clip beam 151 connected to a clip channel 152. A distal end 152a of clip channel 152 has a substantially U-shaped traverse cross-sectional profile with a base wall 152b and a pair of spaced apart upstanding side walls 152c, 152d. The upstanding side walls 152c, 152d of clip channel 152 each have a rounded forward edge 153, a distal retaining step or shoulder 156, and a clip beam recess 157 cut into the upper surface thereof. Clip channel 152 is dimensioned for slidable reception in lumen 144 of working tip 140 such that upstanding side walls 152c, 152d of clip channel 152 are disposed beneath ledges 146d, 146e of side walls 146b, 146c of channel 146 of working tip 140.

Clip beam 151 has a pair of transverse cross beams 155 extending therefrom at a location disposed proximally from distal tip 154 of clip beam 153. When the components of clip 150 are assembled, clip beam 151 is disposed between upstanding side walls 152c, 152d of clip channel 152. Further, clip beam 151 and clip channel 152 are secured or coupled at their proximal ends and separable at their distal ends. The proximal ends of clip beam 151 and clip channel 152 are coupled to one another by retaining bends 158 extending from side walls 152c, 152d. It is contemplated that the proximal ends of clip beam 151 and clip channel 152 may be coupled by a pin, chemical adhesive, weld, or other coupling or laminating method known in the art.

It is contemplated that clip beam 151 is constructed of a flexible, resilient, spring-like-material urging or biasing the assembled clip into a "closed" configuration wherein the distance between the distal ends of the clip beam 151 and clip channel 152 is minimized. It is further contemplated that clip beam 151 may be substantially composed of a permanent material such as a metal (stainless steel or titanium) or a polymer, or a non-permanent material such as bio-absorbable natural or manmade polymer.

Figure 8A:
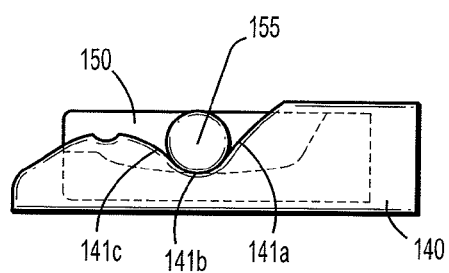
FIGS. 8A-D are schematic illustrations showing a sequence of operation of the clip applier of FIGS. 1-5.

Referring now to FIGS. 8A-8D, a method of using clip applier 100 and suture clip 150 is shown and will be discussed. Initially, as shown in FIG. 8A, a clip 150 is placed or loaded into the lumen 144 of the working tip 140 either by manually inserting clip 150 or by an automatic dispensing mechanism such that the proximal end of clip 150 abuts the distal end of the actuation member 130 and the lateral cross beams 155 of clip 150 rest within cam surfaces 141 of working tip 140. In particular, lateral cross-beams 155 of clip 150 rest in the nadir 141b of cam surfaces 141, between a proximal shoulder 141a and medial incline 141c of cam surface 141. In this initial configuration, plunger 122 is disposed at a proximal most position relative to body 110 such that follower pin 126 is disposed in a first cam channel portion 124a of race 124e (see FIG. 5).

Figure 8B:
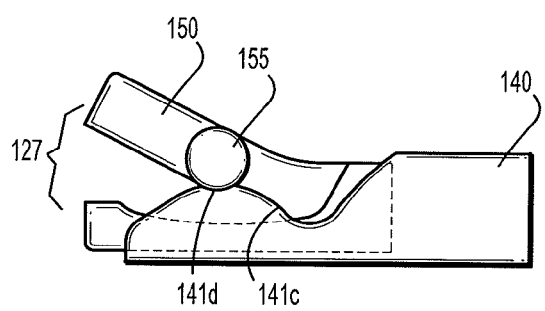

Next, as shown in FIGS. 5 and 8B, as plunger 120 is depressed (i.e., translated distally relative to body 110), follower pin 126 is translated through race 124e from first cam channel portion 124a to second cam channel portion 124b. As follower pin 126 is translated from first cam channel portion 124a to second cam channel portion 124b, an audible/tactile indication is created, in the manner described above.

By depressing plunger 120 to translate plunger 120 distally, actuation member 130 is also translated distally which translates clip 150 distally such that cross-beam 155 is disposed upon distal retaining groove 141d of cam surfaces 141 of working tip 140. The translation of cross beam 155 to distal retaining groove 141d urges clip beam 151 away from beam channel 152 which is retained by ledges 146d, 146e. This separates distal beam tip 154 from clip channel 152 to define opening 127 exposing suture retaining step 156.

Figure 8C:
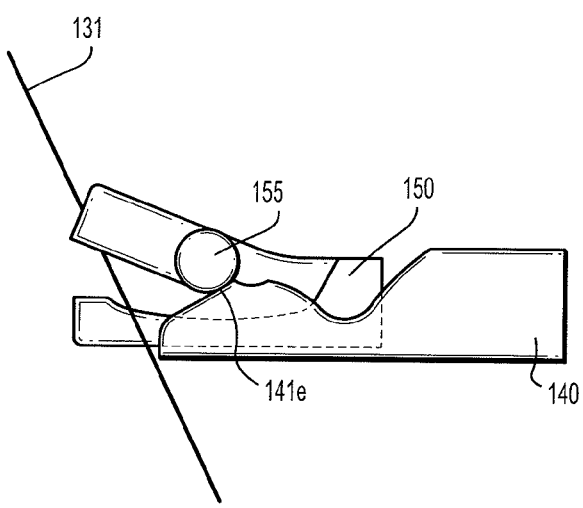

Next, as shown in FIG. 8C, clip applier 100 is maneuvered to capture a suture 131 in opening 127 or a suture 131 is moved into opening 127. With suture 131 disposed within opening 127, plunger 120 is further depressed (i.e., translated distally relative to body 110), thereby translating follower pin 126 through race 124e from second cam channel portion 124b to third cam channel portion 124c. As follower pin 126 is translated from second cam channel portion 124b to third cam channel portion 124c, an audible/tactile indication is created, in the manner described above. As plunger 120 is further depressed, actuating member 130 is further translated in a distal direction thereby translating clip 150 distally until cross beams 155 are moved onto respecting distal ejection shoulders 141e of working tip 140, thus partially closing clip 150 (i.e., approximating clip beam 151 and clip channel 152) onto suture 131.

Next, as plunger 120 is fully depressed, follower pin 126 is translated from third cam channel portion 124c to fourth channel portion 124d. As follower pin 126 is translated from third cam channel portion 124c to fourth cam channel portion 124d, an audible/tactile indication is created, in the manner described above. As plunger 120 is fully depressed, actuating member 130 is fully translated in a distal direction to a distal-most portion of its stroke and ejecting clip 150 from the working tip 140. As clip 150 is fully ejected, suture 131 is captured between clip beam 151 and clip channel 152 of clip 150.

Figure 8D:
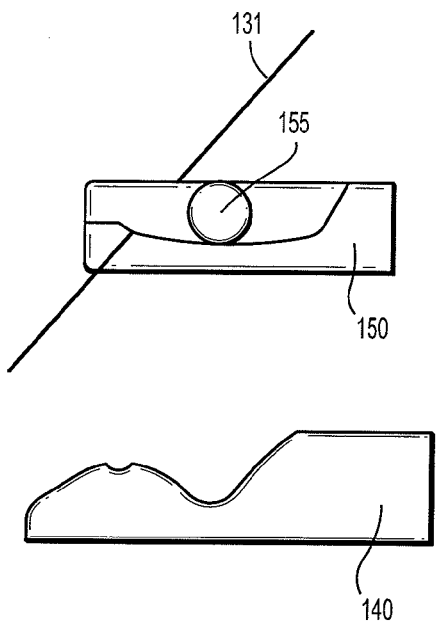

Finally, as shown in FIG. 8D, after clip 150 has been ejected from working tip 140 of clip applier 100, clip 150 securely holds a suture 131 between clip channel 151 and clip beam 152.

Turning now to FIGS. 9-11, an embodiment of a suture clip 250 and a working tip 240 for a clip applier, according to another embodiment of the present disclosure, is shown and described. Working tip 240 has a substantially hook-like profile. In particular, with reference to FIG. 9, the hook-like profile of working tip 240 includes a transverse recess or notch 242 defined by a pair of coincident curved surfaces 242a, 242b, wherein recess 242 is angled or oriented so as to define a proximally extending hook 244. As shown in FIG. 9, working tip 240 further defines a longitudinally axially extending slot 246 configured and dimensioned to receive suture clip 250 therein.

As shown in FIG. 11, suture clip 250 has a substantially rectangular, flattened profile having a distal end portion and proximal end portion. Suture clip 250 includes a pair of spaced apart legs 252, 254 joined to one another by a crown or backspan 256. Legs 252, 254 are separated from one another to define a slot 258 therebetween. Each leg 252, 254 includes a respective angled surface 252a, 254a thereby defining a widened mouth or entry 258a of slot 258 for better receiving a suture 131 therein. A proximal end of slot 258 is dimensioned so as to cinch and retain suture 131 therein. Backspan 256 of suture clip 250 may have a generally V-shaped profile.

In use, as shown in FIGS. 9 and 10, with suture clip 250 loaded into slot 246 of working tip 240, such that mouth 258a of suture clip 250 is disposed proximal of notch 242 of working tip 240, a suture 131 is placed into notch 242 of working tip 240. Preferably, suture 131 is disposed at a base of notch 242. With suture 131 so positioned, an actuating member of the clip applier is manipulated to engage suture clip 250 and urge suture clip 250 in a distal direction. Suture clip 250 is translated distally such that suture is first received in mouth 258a and then advanced into the proximal end of slot 258 of suture clip 250. With suture clip 250 secured to suture 131, the actuation member of the clip applier may be retracted and working tip 240 may be disengaged from suture clip 250.

Turning now to FIGS. 12 and 13, another embodiment of a suture clip, according to the present disclosure, is generally designated as suture clip 350. Suture clip 350 includes a leaf spring 351, a beam 352, and a lever 353. The leaf spring 351 is fixably attached to a proximal end 352b of beam 352 by, for example, a weld. Meanwhile, leaf spring 351 is fixably attached to a distal end 353a of lever 353 by, for example, a weld. Beam 352 defines a traverse groove 352c formed near distal end 353a and being configured to receive a suture therein. It is further contemplated that the attachment of beam 352 to lever 353 and leaf spring 351 may be achieved using a pin, staple, chemical adhesive or other attachment method known in the art.

As shown in FIG. 12, in its neutral configuration or at rest, leaf spring 351 maintains the distal ends 352a, 353a of beam 352 and lever 353 in contact with one another and maintains the proximal ends 352b, 353b of beam 352 and lever 353 separate from one another. With reference to FIG. 13, when a compressive force is applied to proximal ends 352b, 353b of beam 352 and lever 353, the distal ends 352c of beam 352 and lever 353 are separated from one another to open suture clip 350 and define a suture entry area 355. With suture clip 350 in an open condition, a suture 131 may be inserted through suture entry area 355 and captured into the suture retaining groove 352d of beam 352. Once the compressive force is removed, leaf spring acts on beam 352 and lever 353 to close the suture retaining area 355 and secure the suture therebetween.

Turning now to FIG. 14, yet another embodiment of a suture clip, according to the present disclosure, is generally designated as suture clip 450. Suture clip 450 includes a backspan or crown 452 and a pair of spaced apart legs 454, 456 extending therefrom, with each leg 454, 456 being divided into a pair of spaced apart first and second legs 454a, 454b, and first and second legs 456a, 456b, respectively.

As seen in FIG. 14, first and second legs 454a, 454b of leg 454 are separated from one another by a relatively smooth longitudinally extending slot 454c. First and second legs 456a, 456b of leg 456 are separated from one another by a relatively smooth longitudinally extending slot 456c.

Further as seen in FIG. 14, first leg 454a of leg 454 and first leg 456a of leg 456 are separated from one another by a longitudinally extending slot 458 having an undulating or sinusoidal profile. Also, second leg 454b of leg 454 and second leg 456b of leg 456 are separated from one another by a longitudinally extending slot 460 having an undulating or sinusoidal profile.

Suture clip 450 further includes a pair of longitudinally extending channels 462, 464 formed in opposed outer surfaces thereof and extending along an entire length thereof. Each channel 462, 464 is defined by a pair of opposed ledges or shoulders 462a, 462b and 464a, 464b, respectively. Each ledge or shoulder 462a, 462b and 464a, 464b of respective channel 462, 464 includes a respective cam surface 463a, 463b (the cam surfaces of ledge or shoulder 464a, 464b not being visible in FIG. 14) projecting towards one another.

As shown in FIG. 14 and as can be appreciated by one skilled in the art, suture clip 450 may be used with a clip applier that is configured to bias leg 454 and leg 456 apart from one another to receive a suture 131 therebetween. It is contemplated that as suture clip 450 is advanced in a distal direction relative to the clip applier that legs 454, 456 may be biased apart from one another as the cam surfaces 463a, 463b of legs 454b, 456b and the cam surfaces of legs 454a, 456a ride against a corresponding cam surface of the clip applier.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

Those skilled in the art, having the benefit of the teachings of the present invention as herein and above set forth, may effect modifications thereto. Such modifications are to be construed as lying within the scope of the present invention, as defined by the appended claims.

Although specific features of the suture clip applier are shown in some of the drawings and not in others, this is for convenience only as each feature may be combined with any or all of the other features in accordance with the aspects of the present disclosure. Other embodiments will occur to those skilled in the art and are within the following claims.

It is to be understood that the illustrated embodiments are for the purpose of example, and that numerous other configurations of wound dressing systems having a plurality of beads exist. Accordingly, the illustrated and described embodiments are not intended to limit the scope of the inventive subject matter only to those embodiments.

What is claimed is:

1. A suture clip applier, comprising:
    a housing;
    an elongated plunger slidably supported in the housing, the plunger having a distal end portion disposed within the housing and a proximal end portion extending from a proximal end of the housing, wherein the plunger defines a race formed in a surface thereof, the race includes a plurality of portions each defining a cam surface of varying depth;
    a hollow tube extending distally from the housing and defining a lumen therethrough;
    an actuation member having a distal end extending into the hollow tube and a proximal end operatively engaged with the plunger;
    a working tip coupled to a distal end of the hollow tube, wherein the working tip has a substantially U-shaped transverse cross-sectional profile defining a channel having a base wall and a pair of spaced apart side walls, wherein the working tip defines:
        a lower contact surface along an internal face of the base wall, and
        an upper contact surface defined along an upper end surface of each side wall, wherein the upper contact surface of each side wall includes:
            a distal recess formed near a distal end of thereof and a proximal recess formed proximal of the distal recess; and
            an internal retaining surface on both side walls parallel to the base wall,
        wherein the distal end of the actuation member is configured to engage a suture clip loaded into the working tip; and
    a rocker arm having a distal end portion and proximal end portion, the rocker arm has a follower pin extending therefrom near the distal end portion thereof and a retaining pin near the proximal end portion thereof,
        whereby the rocker arm is pivotally attached to the housing by the retaining pin and the follower pin is slidably disposed with in the race of the plunger to modulate the motion of the plunger and actuation member.

2. The clip applier according to claim 1, wherein the race defines four interconnected cam portion, with each cam portion having a start position and an end position and each cam is deepest at its respective start position and shallowest at its respective end position.

3. The clip applier according to claim 1, wherein the rocker arm is elastically deformable laterally from the plunger thereby providing a biasing force upon the follower pin and plunger relative to the body.

4. The clip applier according to claim 1, further comprising finger loops extending from the housing.

5. The clip applier according to claim 1, wherein the actuation member is configured to transmit axial translative forces to the suture clip.

6. The clip applier according to claim 1, further comprising a biasing member disposed within the housing and providing a proximal bias upon the plunger relative to the housing.

7. The clip applier according to claim 6, wherein the biasing member is a coil spring.

8. The clip applier according to claim 1, wherein the distal recess and the proximal recess formed in each vertical side wall are interconnected by a camming surface.

9. A suture clip applier system, comprising:
    a suture clip applier for filing a suture clip onto a suture, the clip applier including:
        a housing;
        an elongated plunger slidably supported in the housing, the plunger having a distal end portion disposed within the housing and a proximal end portion extending from a proximal end of the housing, the plunger defining a race formed in a surface thereof, the race including a plurality of portions each defining a cam surface of varying depth;

a hollow tube extending distally from the housing and defining a lumen therethrough;

an actuation member having a distal end extending into the hollow tube and a proximal end operatively engaged with the plunger;

a working tip coupled to a distal end of the hollow tube, wherein the working tip has a substantially U-shaped transverse cross-sectional profile defining a channel having a base wall and a pair of spaced apart side walls, wherein the working tip defines:
- a lower contact surface along an internal face of the base wall, and
- an upper contact surface defined along an upper end surface of each side wall, wherein the upper contact surface of each side wall includes:
  - a distal recess formed near a distal end thereof and a proximal recess formed proximal of the distal recess; and
  - an internal retaining surface on both side walls parallel to the base wall, wherein the distal end of the actuation member is configured to engage a suture clip loaded into the working tip; and a rocker arm having a distal end portion and proximal end portion, the rocker arm has a follower in extending therefrom near the distal end portion thereof and a retaining pin near the proximal end portion thereof,
whereby the rocker arm is pivotally attached to the housing by the retaining in and the follower in is slidably disposed with in the race of the plunger to modulate the motion of the plunger and actuation member; and a suture clip loadable into and deployable from the working tip, the suture clip including:
an elongated flexible beam having a distal end portion, a proximal end portion, a top surface and a bottom surface, the flexible beam further including a pair of arms extending laterally therefrom; and an elongated rigid channel, wherein the elongated rigid channel has a substantially U-shaped transverse cross-sectional profile with a horizontal base wall and vertical side walls having a distal end portion and proximal end portion, wherein each vertical side wall defines a holding step formed in an upper edge thereof;

wherein the flexible beam and the channel are coupled to one another at their proximal end portions;

wherein the pair of arms of the flexible beam are in registration with a corresponding holding step formed in the upper edge of the vertical side walls; and wherein, as the suture clip is urged in a distal direction relative to the working tip, the flexible beam is splayed apart from the channel to open the suture clip for receipt of a suture therein.

10. The suture clip applier system according to claim 9, wherein the race defines four interconnected cam portion, with each cam portion having a start position and an end position and each cam is deepest at its respective start position and shallowest at its respective end position.

11. The suture clip applier system according to claim 9, wherein the rocker arm of the clip applier is elastically deformable laterally from the plunger thereby providing a biasing force upon the follower pin and plunger relative to the body.

12. The suture clip applier system according to claim 9, wherein the clip applier further comprises a biasing member disposed within the housing and providing a proximal bias upon the plunger relative to the housing.

13. The suture clip applier system according to claim 9, wherein the distal recess and the proximal recess formed in each vertical side wall are interconnected by a camming surface.

14. The suture clip applier system according to claim 9, wherein a proximal end portion of the pair of vertical sides walls of the channel of the suture clip include inwardly projecting lips for retaining the proximal end portion of the beam within the channel.

15. The suture clip applier system according to claim 9, wherein the pair of arms of the suture clip project beyond the pair of vertical side walls of the channel thereof.

* * * * *